(12) United States Patent
Sakaguchi

(10) Patent No.: US 10,188,559 B2
(45) Date of Patent: Jan. 29, 2019

(54) DISPOSABLE DIAPER WITH BUTTOCKS PART STRETCHING UNIT

(71) Applicant: UNICHARM CORPORATION, Shikokuchuo-shi, Ehime (JP)

(72) Inventor: Satoru Sakaguchi, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 618 days.

(21) Appl. No.: 14/647,128

(22) PCT Filed: Nov. 27, 2013

(86) PCT No.: PCT/JP2013/081857
§ 371 (c)(1),
(2) Date: May 26, 2015

(87) PCT Pub. No.: WO2014/084232
PCT Pub. Date: Jun. 5, 2014

(65) Prior Publication Data
US 2015/0305948 A1    Oct. 29, 2015

(30) Foreign Application Priority Data
Nov. 27, 2012  (JP) ................................. 2012-259110

(51) Int. Cl.
*A61F 13/49*     (2006.01)
*A61F 13/494*    (2006.01)
(Continued)

(52) U.S. Cl.
CPC .. *A61F 13/49017* (2013.01); *A61F 13/51466* (2013.01); *A61F 13/5633* (2013.01);
(Continued)

(58) Field of Classification Search
CPC .............. A61F 13/49017; A61F 13/494; A61F 13/4942; A61F 13/5633; A61F 2013/49053
See application file for complete search history.

(56) References Cited

U.S. PATENT DOCUMENTS 5,540,672 A * 7/1996 Roessler ........... A61F 13/49009
604/373
5,649,919 A     7/1997 Roessler et al.
(Continued)

FOREIGN PATENT DOCUMENTS

EP    2856993 A1   4/2015
JP    2-96118 U    7/1990
(Continued)

OTHER PUBLICATIONS

International Search Report dated Dec. 24, 2013, corresponding International Application No. PCT/JP2013/081857.
(Continued)

*Primary Examiner* — Kathryn E Ditmer
(74) *Attorney, Agent, or Firm* — Hauptman Ham, LLP

(57) ABSTRACT

In a disposable diaper, a leg stretching unit stretchable in a longitudinal direction is disposed at an inside of a widthwise direction than a pair of leg opening units. An area between a backside leg opening unit and a straight line passing through a center in the widthwise direction and parallel to the longitudinal direction is larger than an area between a foreside leg opening unit and a straight line passing through a center of the longitudinal direction of the leg opening unit and extending in the longitudinal direction. A buttocks part stretching unit running across a crotch region and the back waistline region and stretchable in the longitudinal direction is disposed at an outside of the widthwise direction than the leg stretching unit. A front end of the buttocks part stretching
(Continued)

unit is positioned more backward than a center of the longitudinal direction of the leg opening unit.

10 Claims, 4 Drawing Sheets

(51) Int. Cl.
  *A61F 13/514*  (2006.01)
  *A61F 13/56*  (2006.01)
  *A61F 13/58*  (2006.01)
  *A61F 13/51*  (2006.01)

(52) U.S. Cl.
  CPC ...... *A61F 13/58* (2013.01); *A61F 2013/4908* (2013.01); *A61F 2013/49025* (2013.01); *A61F 2013/49041* (2013.01); *A61F 2013/49053* (2013.01); *A61F 2013/49088* (2013.01); *A61F 2013/51092* (2013.01); *A61F 2013/588* (2013.01); *F04C 2270/0421* (2013.01)

(56) References Cited

U.S. PATENT DOCUMENTS

| | | | | |
|---|---|---|---|---|
| 6,102,900 | A * | 8/2000 | Roessler | A61F 13/49017 604/385.24 |
| 6,607,515 | B2 * | 8/2003 | Glaug | A61F 13/49 604/385.01 |
| 7,959,618 | B2 * | 6/2011 | Hermansson | A61F 13/496 604/385.01 |
| 2004/0044323 | A1 * | 3/2004 | Roessler | A61F 13/15593 604/385.24 |

FOREIGN PATENT DOCUMENTS

| | | | |
|---|---|---|---|
| JP | 2001212175 A | * | 8/2001 |
| JP | 2004-236832 A | | 8/2004 |
| JP | 2012-61348 A | | 3/2012 |
| JP | 2012-91054 A | | 5/2012 |
| WO | 2013/161952 A1 | | 10/2013 |

OTHER PUBLICATIONS

Written Opinion dated Dec. 24, 2013, corresponding International Application No. PCT/JP2013/081857.
Extended European Search Report in EP Application No. 13857822.4, dated Jun. 27, 2016.
Office Action in CN application No. 201380061899.1, dated Dec. 5, 2016.
Office Action in AU Application No. 2013353131, dated May 25, 2017.
Office Action in ID Application No. P00201503293, dated May 12, 2017, for which English summary is attached.
Office Action in CN Application No. 201380061899.1, dated Jan. 26, 2018, 13pp.
Office Action in CN Application No. 201380061899.1, dated Aug. 21, 2017, 15pp.

* cited by examiner

DISPOSABLE DIAPER WITH BUTTOCKS PART STRETCHING UNIT

RELATED APPLICATIONS

The present application is a national phase of International Application Number PCT/JP2013/081857, filed Nov. 27, 2013, which claims priority to Japanese Application Number 2012- 259110, filed Nov. 27, 2012.

TECHNICAL FIELD

The present invention relates to a disposable diaper.

BACKGROUND ART

Conventionally, there is disclosed a diaper of open type provided with an absorber and side flaps each extending to the outside in a widthwise direction than the absorber, in which a main elastic member is disposed to the outside in a product widthwise direction than the absorber, and a subsidiary elastic member is disposed at the outside in the product widthwise direction than the main elastic member (refer to FIG. 1, FIG. 2, and page 4 to page 5 of Patent Literature 1).

The main elastic member is disposed around a wearer's leg-hole. The subsidiary elastic member is disposed to the outside in the product widthwise direction than the main elastic member in the vicinity of an end of a longitudinal direction of a disposable diaper. The end of the product widthwise direction of the diaper is shrunk by the subsidiary elastic member, and a side leakage of urine or the like can be prevented.

CITATION LIST

Patent Literature

[PTL 1] Japanese Unexamined Utility Model Application Publication No. H2-96118

SUMMARY OF INVENTION

However, the disposable diaper as mentioned above has entailed the following problem.

A wearer's body is not symmetrical at the front and back, and is structured so that a buttocks part which is positioned at a ventral side is longer than that which is positioned at a dorsal side. Although it is an object of the conventional diaper to cover the wearer's body by the side flaps each extending to the outside in the widthwise direction than the absorber, a front waistline region which is disposed at the wearer's dorsal side and a back waistline region which is disposed at the wearer's ventral side are symmetrical to each other. Therefore, the conventional diaper is not disposed along the body line, and is disposed in a state in which the diaper is stretched at the wearer's ventral side. Specifically, a region of a respective one of the side flaps coming into contact with the buttocks part is insufficient, the side flaps are disposed in a convex shape inwardly (to the wearer's body side), and the side flaps are in a stretched state.

If the subsidiary elastic member shrinks in such a state, a stretching portion is involved inside at the time of wearing the disposable diaper or the stretching portion is displaced in a worn state, and there may be a case in which the buttocks part cannot be appropriately covered.

Also, when a disposable diaper of open type is worn, the disposable diaper is disposed at a lower side of a wearer so that a center of a widthwise direction of a leg-hole opening unit matches a center of a crotch part of the wearer, a securely attaching member is pulled up to a front waistline region's side while a buttocks part is enveloped by a back waistline region, and the disposable diaper is fixed around the wearer's waistline by way of the securing attaching member. By wearing the disposable diaper in this manner, the buttocks part can be covered immediately after the disposable diaper has been worn. However, the front waistline and the back waistline are fixed in only a region in which the securing attaching member is joined; and therefore, there is likely to occur a circumstance that a subsidiary elastic member shrinks due to the wearer's motion after the disposable diaper has been worn and then the disposable diaper is involved inside.

Accordingly, the present invention has been made in view of the problem described above, and it is an object of the present invention to provide a disposable diaper which is capable of preventing involvement of an end in a product widthwise direction at the time of wearing while appropriately covering a buttocks part.

A present disclosure is summarized as a disposable diaper (disposable diaper 10) having: a front waistline region; a back waistline region; and a crotch region which is positioned between the front waistline region and the back waistline region, the disposable diaper having: a product longitudinal direction which is oriented from the front waistline region to the back waistline region; and a product widthwise direction which is orthogonal to the product longitudinal direction, the disposable diaper comprising: an absorber running across the crotch region and extending at least one of the front waistline region and the back waistline region; a side flap which run across the front waistline region, the crotch region, and the back waistline region, which is disposed at an outside of the product widthwise direction than the absorber; and a pair of fastening tapes each extending from the back waistline region to the outside of the product widthwise direction of the respective one of the side flaps and securely attaching to the front waistline region; wherein the side flaps each has: an leg opening unit which is concave toward a center in the product widthwise direction of the absorber; and a leg stretching unit which is disposed inside of product widthwise direction than the leg opening unit, which stretches in the product longitudinal direction, wherein the leg opening unit has: a backside leg opening unit which is positioned at a backward than the center of the product longitudinal direction of the leg opening unit; and a foreside leg opening unit which is positioned at a front side than the center of the product longitudinal direction of the leg opening unit, wherein an area between the backside leg opening unit and a straight line which passes through a center in the product widthwise direction and which is in parallel to the product longitudinal direction is larger than an area between the foreside leg opening unit and a straight line which passes the center in the product widthwise direction and which extends in the product longitudinal direction, wherein a buttocks part stretching unit which is disposed so as to run across the crotch region and the back waistline region and which stretches in the product longitudinal direction is disposed at the outside of the product widthwise direction than the leg stretching unit, and wherein a front end of the buttocks part stretching unit is positioned at a backward than a center of the product longitudinal direction of the leg opening unit.

DESCRIPTION OF EMBODIMENTS

Figure 1:
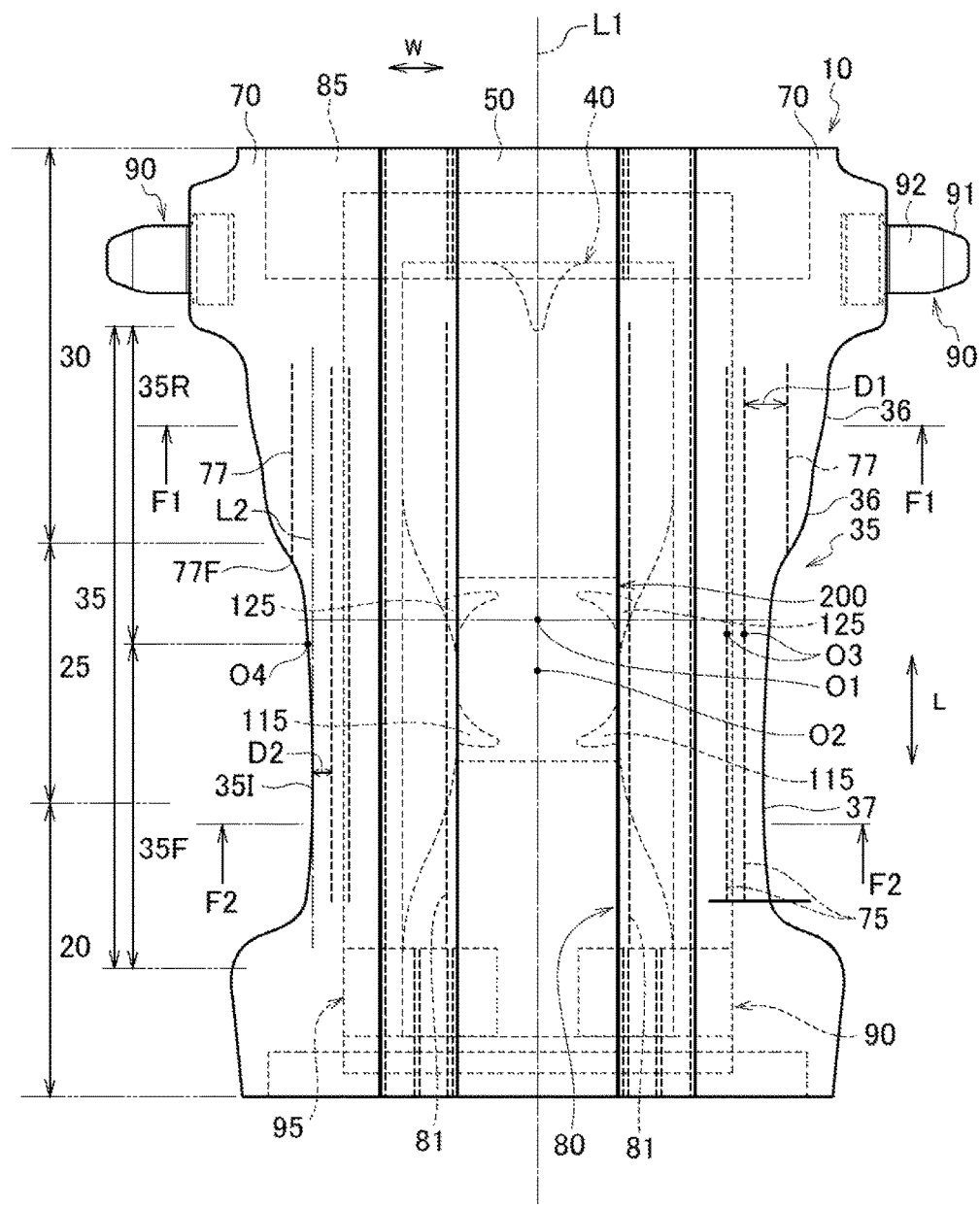
FIG. 1 is an exploded plan view of a disposable diaper according to the embodiment.

Next, embodiments of a disposable diaper 10 according to the present invention will be described with reference to the drawings. It is to be noted that in the following description of the drawings, same or similar constituent elements are designated by same or similar reference numerals. However, it should be kept in mind that the drawings are schematic representations and are not drawn to scale unless otherwise specified. Moreover, the drawings do not necessarily reflect the actual dimensional relationships and ratios of component.

Therefore, specific dimensions or the like should be determined in consideration of the following description. In addition, relations or ratios among such dimensions may be different from one drawing to another.

1. Overall Schematic Structure of Disposable Diaper

Figure 2:
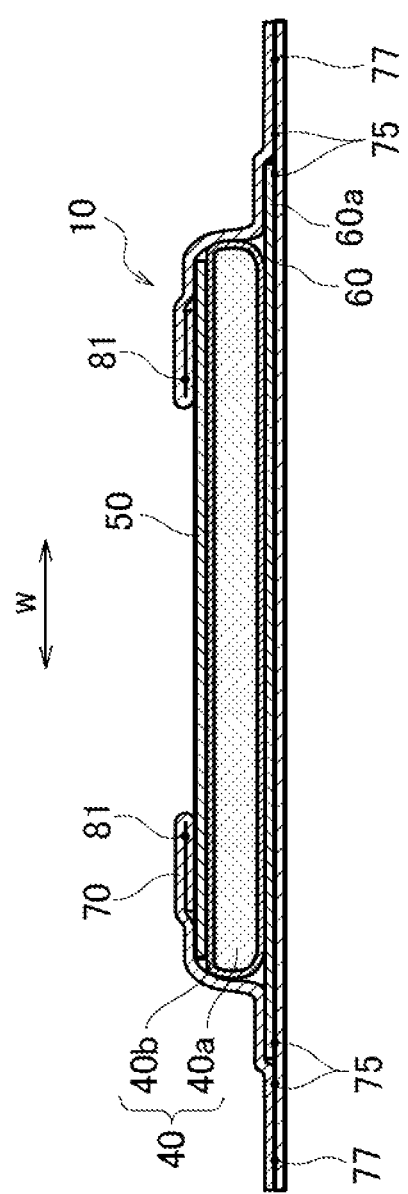
FIG. 2 is a sectional view of the disposable diaper, taken along the line F1-F1 shown in FIG. 1.
Figure 3:
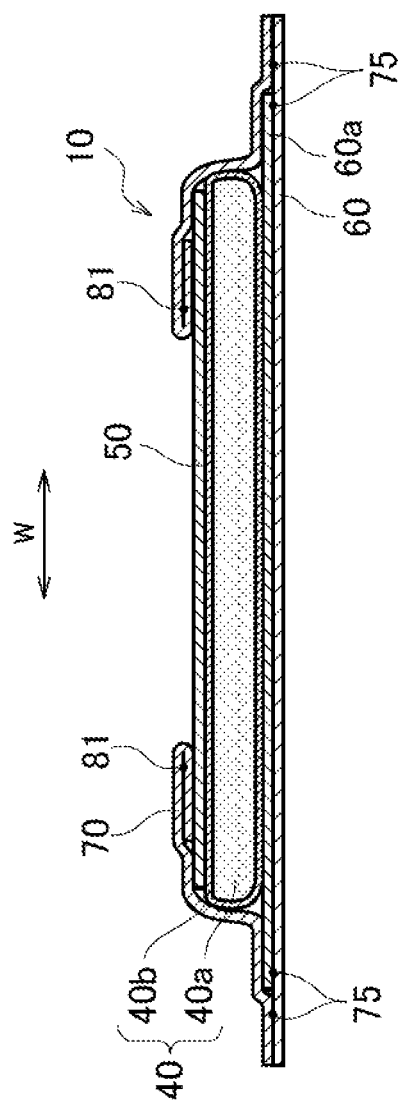
FIG. 3 is a sectional view of the disposable diaper, taken along the line F2-F2 shown in FIG. 1.

FIG. 1 is an exploded plan view of the disposable diaper according to the embodiment. FIG. 2 is a sectional view of the disposable diaper 10, taken along the line F1-F1 shown in FIG. 1. FIG. 3 is a sectional view of the disposable diaper, taken along the line F2-F2 shown in FIG. 1. The exploded views shown in FIG. 1 is views of a state in which an elastic member 81 of a leg stretching unit 75 and a leg side gather 80 is stretched up to a state in which wrinkles of the topsheet 50 or the side flaps 70 or the like constituting the disposable diaper are not formed.

The disposable diaper 10 has a front waistline region 20, a crotch region 25, and a back waistline region 30. The front waistline region 20 is a portion which comes into contact a front waistline part (a dorsal portion) of a wearer. Also, the back waistline region 30 is a portion which comes into contact with a back waistline part (a ventral portion) of the wearer. The crotch region 25 is positioned between the front waistline region 20 and the back waistline region 30.

In the present embodiment, the direction from the front waistline region 20 towards the back waistline region 30 is called the product longitudinal direction L, and the direction perpendicular to the product longitudinal direction L is called the product widthwise direction W.

The disposable diaper 10 includes an absorber 40 running across the crotch region 25 and extending from the crotch region 25 to at least one of the front waistline region 20 and the back waistline region 30. The absorber 40 is configured by an absorbent core 40a and a core wrap 40b.

The absorbent core 40a is same as in the conventional disposable diaper, and can be configured appropriately by using popular components and materials, such as ground pulp and high absorbent polymer. The absorbent core 40a is wrapped by the sheet-like core wrap 40b.

The core wrap 40b is a sheet for wrapping the absorbent core 40a. A part of at least the skin surface side of the core wrap 40b is configured by various nonwoven fabrics or a tissue sheet having permeability. For example, an airthrough nonwoven cloth, a spunbond nonwoven cloth, or an SMS (spunbond-meltblown-spunbond) nonwoven cloth having a mass of approximately 10 to 30 g/m$^2$, or a tissue sheet having a mass of approximately 10 to 30 g/m$^2$ can be used.

On the top side (skin contact surface side) of the absorber 40 is provided the liquid-permeable topsheet 50. Furthermore, on the back side (non-skin contact surface side) of the absorber 40 is provided a liquid-impermeable backsheet 60a. On the back side (non-skin contact surface side) of the backsheet 60a is provided an exterior sheet 60.

A side flap 70 is provided in each side edge in the product widthwise direction W of the absorber 40. The side flaps 70 are running across the front waistline region 20, the crotch region 25 and the back waistline region 30 and are disposed at outside in a product widthwise direction than the absorber 40. The side flaps 70 are made of one or two or more pieces of nonwoven fabrics overlapping one another.

At the side flaps 70 of the disposable diaper 10, a pair of leg opening units 35 are respectively formed. The leg opening units 35 are portions which are respectively provided at side ends in the product widthwise direction of the disposable diaper and which are disposed along the wearer's leg-hole in a state in which the disposable diaper has been worn by the wearer. The leg opening units 35 each are concave toward a center in the product widthwise direction of an absorbent main body.

The leg opening units 35 each have: a backside leg opening unit 35R which is positioned at a backward than a center O4 in a product longitudinal direction of the respective opening unit; and a foreside leg opening unit 35F which is positioned at a front side than the center in the product longitudinal direction of the leg opening unit. An area between the backside leg opening unit 35R and a straight line which passes though the center in the product widthwise direction and which is in parallel to the product longitudinal direction is larger than a region between the foreside leg opening unit 35F and a straight line which passes through the center in the product widthwise direction and which is in parallel to the product longitudinal direction. The area is an area in a stretched state in which the leg stretching unit 75 and an elastic member 81 of a leg side gather 80 has been stretched to a state in which wrinkles of the topsheet 50 and the side flaps 70 or the like constituting the disposable diaper cannot be visually recognized.

Also, at the pair of side flaps 70, fastening tapes 90 are respectively provided. The fastening tapes 90 each extend along a product widthwise direction W in the back waistline region 30, and are securely attached to a non-skin contact surface of the front waistline region 20 to thereby retain the disposable diaper 10 at the wearer's body.

The target unit 95 is provided in a pair, is disposed on the non-skin contact surface in the front waistline region, and is structured so that the pair of fastening tapes 90 are respectively securely attached thereto.

In the embodiment, a waistline retaining unit is composed of the front waistline region 20, the back waistline region 30, and the fastening tape 90. The waistline retaining unit of the back waistline region 30 is a range extending in the product widthwise direction from a region in which an engagement member of the fastening tape 90 has been provided. The waistline retaining unit of the front waistline region 20 is a range extending in the product widthwise direction from a region in which the target unit 95 has been provided.

Also, the disposable diaper 10 is provided with a crotch stretching unit 200 which is disposed in a region overlapping with the absorber of the crotch region 25. It is to be noted that a structure of the crotch stretching unit 200 will be described later in detail.

At the side flaps 70, there are provided a pair of leg stretching units 75 which are disposed inside of product widthwise direction than the leg opening units 35 and which are stretchable in the product longitudinal direction L.

The leg stretching unit 75 is longer than the crotch stretching unit 200 in the product longitudinal direction L, and is provided more outside than the crotch stretching unit 200 in the product widthwise direction W.

It is sufficient if the leg stretching unit 75 is structured so that the leg opening unit 35 can be stretched in the product longitudinal direction, and the leg stretching unit may be disposed along the leg opening unit 35 or may be disposed in a state in which a part of the leg stretching unit is inclined as a guide for the leg opening unit 35.

Also, at the outside in the product widthwise direction than the leg stretching unit 75, there is disposed a buttocks part stretching unit 77 which is disposed across the crotch region 25 and the back waistline region 30 and which is stretchable in the product longitudinal direction.

It is to be noted that the leg stretching unit 75 and the buttocks part stretching unit 77 are portions which are substantially shrunk in the product longitudinal direction by string rubber or the like, and are based on a conceptual idea excluding a portion at which a stretchable sheet has been disposed in a state in which a shrink force is not attained. It is also to be noted that a structure of a respective one of the leg stretching unit 75 and the buttocks part stretching unit 77 will be described later in detail.

Furthermore, a pair of leg side gathers 80 extending along the product longitudinal direction L are provided at the inner side of the pair of leg stretching units 75 (towards the center in the product widthwise direction W). The leg side gathers 80 are provided at inside ends in the product widthwise direction of the side flap 70, and are rising-type stretching gathers disposed to be inner in the product widthwise direction than the leg stretching unit 75. The leg side gathers 80 are disposed at inside ends in the product widthwise direction than the leg stretching units 75. As the leg side gathers 80, a known structure in the prior art can be employed, and specifically, these gathers may be composed of a sheet material other than that for the side flap 70.

Also, between the pair of fastening tapes in the product widthwise direction, a waistline stretching unit 85 which is stretchable in the product widthwise direction is provided. The waistline stretching unit 85 shrinks between the fastening tapes in the product widthwise direction.

In the embodiment, the waistline stretching unit 85 is composed of an elastic sheet. Although members constituting the waistline stretching unit 85 are not limited in particular, it is preferable to employ a member which is as thin as possible, which is low in bending rigidity, and which is small in widthwise inclusion rate. The waistline stretching unit 85 is composed of a material with a low bending rigidity, whereby the waistline stretching unit 85 is made bendable along the body, and the waistline stretching unit 85 can be fitted along the body without applying a load on the wearer's body. Also, the waistline stretching unit 85 is composed of a material with a small widthwise inclusion rate to thereby restrain the shrink in the product longitudinal direction of the disposable diaper in a case where the disposable diaper has been stretched in the product widthwise direction, and to be thereby able to restrain pulling down to the crotch side of the disposable diaper around the waistline of the wearer.

In the embodiment, as the waistline stretching unit 85, an elastic film of 20 g/m$^2$ to 45 g/m$^2$ in basis weight was employed.

The waistline stretching unit 85 is pulled to 1.5 times to 2.5 times of a length in a non-stretched state (a natural state) and subsequently is adhesively bonded with an exterior sheet 60 by hot melt adhesive agent or a heating treatment or the like.

In the embodiment, the waistline stretching unit 85 is disposed between the exterior sheet 60 and a backsheet 60a. However, in a structure in which a core wrap 40b extends to the outside in the product longitudinal direction than an absorbent core 40a, the waistline stretching unit 85 may be disposed between the core wrap 40b and the backsheet 60a or the exterior sheet 60. A position of the waistline stretching unit is not limited in particular. Also, in a region in which no absorber is disposed, this waist stretching unit may be disposed between a side flap 70 and the backsheet 60a or the exterior sheet 60.

It is to be noted that, although the waistline stretching unit according to the embodiment is structured so as to stretch in the product widthwise direction, this waistline stretching unit may be structured so as to stretch in the product widthwise direction and the product longitudinal direction.

The fastening tape 90 is installed in the region of the side flaps 70 corresponding to the back waistline region 30. The fastening tape 90 is provided with: a base sheet 91 coupled with the side flap 70; and a hook sheet 92 in which engagement hooks (not shown) as a plurality of engagement members are provided, and which is fixed to the base sheet 91. The hook sheet 92 is a region in which the engagement members are provided, and the waistline retaining unit mentioned above is a region extending in the product widthwise direction W from the hook sheet 92.

The hook sheet 92 is fixed to specifically, joined with, the base sheet 91. The hook sheet 92 and the base sheet 91 are desired to be joined such that the rigidity of the fastening tape 90 does not become more than necessary. Specifically, the hook sheet 92 and the base sheet 91 are desired to be joined by a hot-melt adhesive applied intermittently in dot shape, line shape, or spiral shape. The hook sheet 92 and the base sheet 91 may also be joined with a heat seal.

The base sheet 91 is configured by one layer of nonwoven fabric or two or more plurality of layers of nonwoven fabric layered on each other. A nonwoven fabric manufactured by a manufacturing method such as spun bond (SB) or spun bond-melt blown-spun bond (SMS) can be used as the base sheet 91. The basis weight of the nonwoven fabric (or a basis weight in the case of a plurality of layers) configuring the base sheet 91 is between 30 and 120 g/m$^2$, and desired to be between 40 and 90 g/m$^2$.

The target unit 95 is provided on a non-skin contact surface of the exterior sheet 60 of the front waistline region 20. The target unit 95 is configured so as to be hooked by an engagement hook of a fastening tape, and functions as a loop of an engagingly locking system of hook and loop. As the target unit, for example, air-through nonwoven cloth can be employed.

As the target unit 95, for example, there can be employed a textile nonwoven cloth or a polyolefin-based thermoplastic synthetic resin film made of polyolefin-based thermoplastic synthetic resin fibers. Also, a loop mounted to the target unit 95 can be formed of a polyolefin-based thermoplastic synthetic resin.

Further, as the target unit 95, there may be employed a bulky nonwoven cloth, a part of which is embossed to thereby prevent scuffing of a surface of the nonwoven cloth.

Furthermore, the exterior sheet 60 of the disposable diaper is formed of a nonwoven cloth, and a symbol indicating a mounting position of the fastening tape 90 is printed on a surface of a non-skin contact side of the backsheet 60*a* or the exterior sheet 60. Alternatively, a symbol sheet is also disposed at the non-skin contact side of the backsheet 60*a* or the exterior sheet 60, whereby a target unit can be formed.

Still furthermore, an area between the backside leg opening unit and a straight line L1 which passes through the center in the product widthwise direction and which is in parallel to the product longitudinal direction is larger than an area between the foreside leg opening unit and the straight line L1 which passes through in the product widthwise direction and which is in parallel to the product longitudinal direction. Therefore, a side flap which is positioned at the backward than the center in the product longitudinal direction of the leg opening unit extend to the outside in the product widthwise direction than a side flap which is positioned at the front side than the center in the product longitudinal direction of the leg opening unit.

It is to be noted that the straight line L1 which passes through the center in the product widthwise direction and which is in parallel to the product longitudinal direction is a straight line L1 which passes through the center in the product widthwise direction of the disposable diaper and which is in parallel to the product longitudinal direction.

The wearer's body is not symmetrical at the front and back, and a surface area of the ventral side is larger than a surface area of the dorsal side. This is because the buttocks part exists outside at the ventral side of the wearer. Also, in a state in which the wearer has worn the disposable diaper, the center in the product longitudinal direction of the leg opening unit is prone to be at a position which corresponds to the center in the product longitudinal direction of the wearer's crotch. For example, if an area between the backside leg opening unit that is positioned at the backward than the center in the product longitudinal direction of the leg opening unit and the straight line that passes through the center in the product widthwise direction and which is in parallel to the product longitudinal direction is equal to an area between the foreside leg opening unit that is positioned at the front side than the center in the product longitudinal direction of the leg opening unit and the straight line that passes through the center in the product widthwise direction and that is in parallel to the product longitudinal direction, or alternatively, if the area between the backside leg opening unit and the straight line that passes through the center in the product widthwise direction and which is in parallel to the product longitudinal direction is smaller than the area between the foreside leg opening unit and the straight line that passes through the center in the product widthwise direction and which is in parallel to the product longitudinal direction, the disposable diaper cannot be disposed so as to cover the body that is asymmetrical at the front and back, the diaper is in a stretched state at the wearer's ventral side or is in a twisted state at the wearer's dorsal side.

If the positions in the product widthwise direction of a side flap which is positioned at the backward than the center in the product longitudinal direction of the leg opening unit and a side flap which is positioned at the front side than the center in the product longitudinal direction of the leg opening unit are substantially the same as each other, and these side flaps are in a stretched state at the wearer's ventral side, the leg opening unit 35 at the back waistline region's side turns up while the diaper is worn, and there may be a case in which the wearer's buttocks part is exposed. Also, there does not exist a sufficient area in which the buttocks part can be covered; and therefore, an end in the product widthwise direction in the back waistline region is involved inside at the time of wearing the disposable diaper, and there may be a case in which the wearer's buttocks part is exposed.

However, the side flap that is positioned at the backward than the center in the product longitudinal direction of the leg opening unit extends to the outside in the widthwise direction than the side flap that is positioned at the front side than the side flap that is positioned at the front side than the center in the product longitudinal direction of the leg opening unit; and therefore, the disposable diaper can be disposed so as to cover the body that is asymmetrical at the front and back, and the disposable diaper can be disposed so as to correspond to the wearer's body.

At the backside leg opening unit 35R, a plurality of convex units 36, a respective one of which is in a convex shape to the outside in the product widthwise direction, are formed. The convex units 36 are portions extending to the outside in the product widthwise direction than the regions at the front and back of the leg opening unit. The leg opening unit 35 is a site which abuts against leg feed of the wearer, and is also a portion which is easily included to the inside of the disposable diaper 10. Therefore, it is preferable that the leg opening unit 35 cover the body more widely, and in particular, it is desirable that the backside leg opening unit 35R be disposed so as to widely cover the body. The convex units 36 are provided, whereby an area of a portion of the backside leg opening unit 35R is increased, and as shape thereof is formed outward in a convex shape, whereby the buttocks part can be widely covered.

Further, at the backside leg opening unit 35R, in particular, at a rear part of the backside leg opening unit 35R, a stress easily concentrates; and therefore, it is preferable that a pressure to a skin can be dispersed by forming the convex units 36. Specifically, a position which is close to a proximal end of the fastening tape 90 is a portion at which a stress easily concentrates and which overlaps at the front and back at the time of wearing the disposable diaper 10; and therefore, it is preferable to form a convex shape so as to be able to disperse the pressure to the skin.

At the foreside leg opening unit 35F, a concave unit is formed in a concave shape to the inside in the product widthwise direction. The concave unit 37 is a portion which is in a concave shape to the inside in the product widthwise direction than the regions at the front and back of the leg opening unit. The concave unit 37 is in the concave shape; and therefore, this concave unit is easily taken along the wearer's groin part. Thus, the side flaps 70 and the leg stretching unit 75 fit to the wearer, and a region from the front waistline region 20 to the crotch region 25 of the disposable diaper 10 can be stably taken along the body irrespective of whatsoever the wearer's motion may be. For example, even in a case where a motion is made in such an extent that the width of the absorber 40 is reduced by the motion of the wearer's legs, the concave unit 37 continuously fits to the groin region, and a wide state thereof can be maintained without reduction of the width of the absorber 40. The convex units 36 and the concave unit 37 need to be taken along the wearer's body in addition to mitigation of the pressure to the skin.

2. Structure of Leg Stretching Unit and Buttocks Part Stretching Unit

A leg stretching unit 75 is disposed along the product longitudinal direction L at the outside of the product widthwise direction than the absorber 40, and is structured so as to be stretchable in the product longitudinal direction L.

The leg stretching unit 75 is composed of a predetermined number of elastic members (two elastic members in the example of FIG. 1). The elastic members according to the embodiment each are made of a polyurethane elastic fiber or a natural rubber. A buttocks part stretching unit 77 is composed of a predetermined number of elastic members (one elastic member in the example of FIG. 1). The elastic member according to the embodiment is made of a polyurethane elastic fiber or a natural rubber.

Also, the elastic member constituting the buttocks part stretching unit 77 of the embodiment is a string rubber which is disposed along the product longitudinal direction. Therefore, the side flaps 70 can be taken along the wearer's buttocks part that is convex in shape by uniformly shrinking the entire region in which the buttocks part stretching units of the side flaps 70 are provided; and therefore, the buttocks part can be covered without turning up of the region.

A center O3 of the product longitudinal direction of the leg stretching unit 75 is positioned at the front side than a center O1 of the product longitudinal direction of the disposable diaper in a stretched state of the disposable diaper. Also, in the stretched state of the disposable diaper, a center O4 of the product longitudinal direction of the leg opening unit 35 is positioned at the front side than the center O1 of the product longitudinal direction of the disposable diaper.

Thus, the center O3 of the product longitudinal direction of the leg stretching unit 75 and the center O4 of the product longitudinal direction of the leg opening unit 35 each are disposed at the front side than the center O1 of the product longitudinal direction of the disposable diaper, whereby a length of the product longitudinal direction L of the back waistline region 30 can be determined to be larger than a length of the product longitudinal direction L of the front waistline region 20 in a state in which the disposable diaper has been worn while the center O3 of the product longitudinal direction of the leg stretching unit 75 and the center O4 of the product longitudinal direction of the leg opening unit 35 each are aligned with the center of the product longitudinal direction of the body.

As described above, the wearer's body is not symmetrical at the front and back, and is structured so as to be longer at the ventral side than at the dorsal side. For example, the length of the product longitudinal direction L of the back waistline region 30 and the length of the product longitudinal direction of the front waistline region 20 are equal to each other, and the disposable diaper is not disposed along the body line that is asymmetrical at the front and back.

In particular, in a case where motion of the wearer arises (in particular, when the wearer lifts up his or her legs, stands up, or sits down), the stretching quantity of a skin of a surface of the wearer's body (a variation quantity of a length) is greater at the ventral side (the buttocks part) than at the dorsal side. Therefore, for example, if the length of the product longitudinal direction L of the back waistline region 30 in a natural state of the disposable diaper 10 and the length of the product longitudinal direction L of the front waistline region 20 in the natural state of the disposable diaper 10 are equal to each other, the diaper is in a stretched state at the wearer's ventral side.

However, in so far as the disposable diaper according to the embodiment is concerned, the length of the product longitudinal direction L of the back waistline region 30 in the natural state of the disposable diaper 10 can be determined to be longer than the length of the product longitudinal direction L of the front waistline region 20 in the natural state of the disposable diaper 10; and therefore, the periphery of the buttocks part of the wearer can be appropriately covered. Therefore, even in a case where motion of the wearer arises, it is possible to restrain a circumstance that the front waistline region 20 and the back waistline region 30 of the disposable diaper 10 move in an orientation taken along the product longitudinal direction L while being influenced by the motion of the wearer's skin, and the buttocks part can be appropriately covered.

Further, the center O3 of the product longitudinal direction of the leg stretching unit 75 and the center O4 of the product longitudinal direction of the leg opening unit 35 each are disposed at the front side than the center O1 of the product longitudinal direction of the disposable diaper, whereby the leg opening unit can be formed to be close to the front side (close to the dorsal side). The wearer's legs extend toward an orientation which is close to the front side of the body. In a state of being engaged by way of the fastening tape 90, the leg opening unit 35 is at a position close to the front side; and therefore, a diaper which is more suitable for the wearer's body is obtained. Thus, the wearer easily moves his or her legs at the time of wearing the disposable diaper, and the back waistline region can be hardly stretchable.

Figure 4:
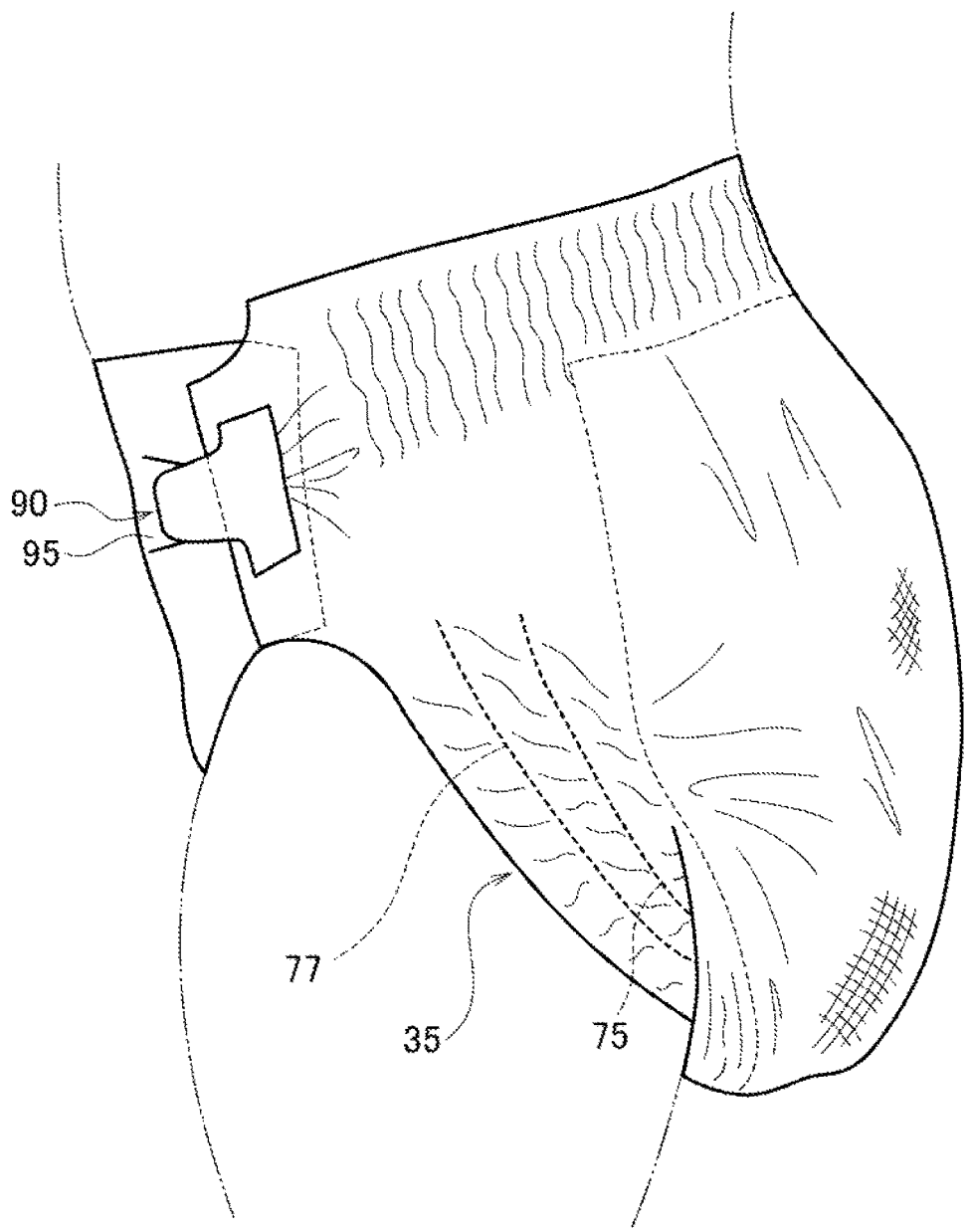
FIG. 4 is a view showing a state wearing to the wearer the disposable diaper according to the present embodiment.

Also, the buttocks part stretching unit 77 is disposed so as to run across the crotch region 25 and the back waistline region 30, and a front end 77F of the buttocks part stretching unit is positioned at the backward than the center of the product longitudinal direction of the leg opening unit 35. Therefore, the back part of the leg stretching unit and the outside region of the product widthwise direction are shrunk by the buttocks part stretching unit 77, and the vicinity of the leg opening unit in the back waistline region (the end at the crotch side of the buttocks part) can be pulled up backward and outside in the widthwise direction. FIG. 4 is a view schematically showing a state in which the disposable diaper has been worn.

For example, in general, when the disposable diaper is worn, in a state in which the crotch region of the disposable diaper abuts against the wearer's crotch, the disposable diaper is pulled up in the product longitudinal direction, and is fixed by the fastening tape or the like. By wearing the disposable diaper in this manner, the disposable diaper is pulled up between the securely attached portion of the fastening tape and the crotch region, and there may be a case in which the leg opening unit 35 is not disposed along the wearer's leg-hole.

In particular, in so far as the buttock part's side is concerned, an area of the buttocks part is large in comparison with the wearer's dorsal side; and therefore, the end of the product widthwise direction in the back waistline region is involved inside at the time of wearing the disposable diaper, and there is an apprehension that a part of the buttocks part is exposed. However, the disposable diaper can be made close to the back waistline region 30 by way of the buttocks part stretching unit 77, and a failure of exposure of the wearer's buttocks part can be restrained.

In the stretched state of the disposable diaper 10, it is desirable that a distance D1 between the buttocks part stretching unit 77 and the leg stretching unit 75 in the product widthwise direction be 10 mm to 30 mm. For example, if the distance between the buttocks part stretching unit 77 and the leg stretching unit 75 is larger than 30 mm, the buttocks part stretching unit 77 and the leg stretching unit 75 shrinks respectively independently, and the buttocks part stretching unit 77 and the leg stretching unit 75 hardly move together. However, in the case where the distance between the buttocks part stretching unit and the leg stretching unit in the product widthwise direction in the stretched state of the disposable diaper 10 is 10 mm to 30 mm, the buttocks part stretching unit 77 and the leg stretching unit 75 easily move together. For example, if only the buttocks part stretching unit shrinks independently, it is considered that a shrink portion is involved inside or falls down when the diaper is worn. However, the buttocks part stretching unit and the leg stretching unit move together, whereby it is possible to restrain falling down of the buttocks part stretching unit to the inside.

It is to be noted that measurement of the "length" in the specification is carried out by the following measurement method.

In a case where the disposable diaper 10 was sealed in a package or the like, the diaper was taken out from the package, and in that state, a sample having been left for 12 hours under an atmosphere of 20 degrees Centigrade±2 degrees Centigrade and 60%±5% RH in relative humidity was employed.

Next, by employing a spring measure (tape: glass fiber-containing vinyl chloride-coated) available from Sinwa Rules Co., Ltd., so as to be taken along a site targeted to be measured, a length of this state of the disposable diaper 10, namely, a length of the leg stretching unit 75 in the natural state of the disposable diaper 10 was measured. Also, in so far as a length in a stretched state is concerned, a length of the leg stretching unit 75 was measured when the disposable diaper 10 was stretched up to a state in which wrinkles exerted by the elastic member cannot be visually observed from the natural state.

Here, with respect to 10 samples, the measurement as mentioned above was carried out in their respective states, and an average value thereof was defined as a length. Based on the thus measured length, an area can be computed.

The leg opening unit 35 is in a convex shape from the outside in the product widthwise direction to the inside in the product widthwise direction, and a distance D2 between an inside end 35I which is positioned at the most inside in the product widthwise direction in the leg opening unit 35 in the stretched state of the disposable diaper 10 and the leg stretching unit 75 is shorter than a distance in the product widthwise direction between the leg stretching unit and the buttocks part stretching unit, and is 15 mm or less.

If the distance between the inside end 35I of the leg opening unit 35 in the stretched state of the disposable diaper 10 and the leg stretching unit 75 is larger than 15 mm, the shrink force exerted by the leg stretching unit 75 does not act on a region leading up to the inside end of the leg opening unit 35, and there is an apprehension that the leg opening unit 35 cannot be appropriately shrunk by the leg stretching unit 75. Also, the inside end 35I of the leg opening unit 35 is a portion which is sandwiched by the wearer's legs in the worn state and which comes into intimate contact with the wearer. The distance between the inside end 35I of the leg opening unit 35 and the leg stretching unit is 15 mm or less, whereby at least a portion of the leg opening unit coming into contact with the wearer is shrunk, and can be disposed along the wearer's leg-hole.

At the side flaps 70, frill-like shrinking units which have been shrunk by the leg stretching unit 75 and the buttocks part stretching unit 77 are formed. The frill-like shrinking units can be brought into intimate contact with the body by the leg stretching unit 75 and the buttocks part stretching unit 77. Also, the distance between the inside end 35I that is positioned at the innermost of the product widthwise direction in the leg opening unit and the leg stretching unit is shorter than the distance between the leg stretching unit and the buttocks part stretching unit; and therefore, the involvement of the inside end of the leg opening unit is restrained by the leg stretching unit, the buttocks part stretching unit is disposed from the crotch region to the back waistline region, and a shape in which the entire region has widened is easily maintained in the region in which the buttocks part stretching unit of the side flap has been disposed.

Further, the frill that is formed of the leg stretching unit 75 and the buttocks part stretching unit 77 shrinks in the product longitudinal direction; and therefore, the frill (wrinkle) extends along the product widthwise direction. While being supported by this frill (wrinkle), it is possible to prevent the involvement to the inside in the widthwise direction of the end of the product widthwise direction in the back waistline region.

Furthermore, the buttocks part stretching unit 77 may be in a stretched state all over the region or regions of both ends thereof may be in a non-stretched state. For example, the regions of both ends of the buttocks part stretching unit 77 (a region of 10 mm or less and 2 mm or more, more preferably, a region of 5 mm or less and 2 mm or more) is in a non-stretched state, whereby a wrinkle-restrained state can be established in the vicinity of the backside leg opening unit 35R. Therefore, the vicinity of the backside leg opening unit 35R can be taken along the body in a more gapless manner. Also, an adhesive agent such as an HMA adhesive agent is disallowed to be provided at an end of the buttocks part stretching unit 77 to thereby able to soften an edge of the backside leg opening unit 35R at which the end of the buttocks part stretching unit 77 is positioned.

The inside end 35I of the leg opening unit, in the natural state of the disposable diaper 10, is positioned on a centerline L2 which passes through a center in the product widthwise direction between the leg stretching unit and the buttocks part stretching unit and which is taken along the product longitudinal direction. According to such a structure, the inside end of the leg opening unit is pulled up by the leg stretching unit and the buttocks part stretching unit, and the involvement of the inside end of the leg opening unit can be prevented. Therefore, the inside end of the leg opening unit can be disposed so as to be taken along the body.

The leg stretching unit 75 is disposed between the side flap 70 and the exterior sheet 60. Alternatively, in a region in which the backsheet 60a disposed between the absorber 40 and the exterior sheet 60 is provided, the leg stretching unit 75 is disposed between the backsheet 60a and the side flap 70.

The stretch rate of the leg stretching units 75 is preferably 1.7 to 2.4 times. For example, in the first embodiment, the stretch rate of the leg stretching units 75 may be set to 1.9 to 2.2 times. It is to be noted that a ratio of expansion and contraction means degree of expansion and contraction of the leg stretching unit and is determined as follows.

Ratio of expansion and contraction=(length in the expansion and contraction direction of the leg stretching unit in the stretched state)/(length in the expansion and contraction direction of the leg stretching unit in a natural state)

It is to be noted that the stretch rate as used herein is to be measured as described below, for example.

Firstly, in a case where the disposable diaper 10 is inserted into a package, for example, the disposable diaper 10 is then taken out of the package. Next, a disposition region of the leg stretching unit is notch. At this time, an area including the exterior sheet joined with the leg stretching unit is also notch. An extension rate of a sample of the leg stretching unit after notch is measured, and the extension rate of the leg stretching unit is measured.

Each of the samples is left as is for 60 minutes in an atmospheric environment of 20 degrees Centigrade±2 degree Centigrade and a relative humidity of 60%±5% RH, and a length of the leg stretching unit is measured along a stretching direction. This length is defined as "a length of the leg stretching unit in a natural state".

Secondly, the length in the stretching direction of the desired region of the open-type disposable diaper in this state (that is, in the natural state), and the length in the stretching direction of the desired region, when the open-type disposable diaper is stretched from its natural state until wrinkles caused by the elastic members cannot be visually checked on the non-stretchable sheet, are measured. This length is defined as "a length of the leg stretching unit in the stretched state".

By employing these results of measurement and then carrying out computation by the formula mentioned above, the stretch rate is measured.

3. Shape of Crotch Stretching Unit

Hereinafter, a shape of the crotch stretching unit 200 will be explained. The crotch stretching unit 200 is configured to maintain a flat shape in a part of the crotch region at the time of putting the disposable diaper on a wearer, as compared to the other part of the absorber 40. The crotch stretching unit 200 is stretchable configured at least in the product longitudinal direction L or in the product widthwise direction W.

The crotch stretching unit 200 is provided so as to be individually independent of the leg stretching unit 75, and at a position which overlaps with the absorbent core 40a (at a position between the core wrap 40b enveloping the absorbent core 40a and the backsheet 60a), this crotch stretching unit is structured so as to shrink 60% or more of the length in the product widthwise direction of the absorbent core 40a at the position that overlaps therewith. Thus, a portion at which the absorbent core 40a has been disposed is shrunk by the crotch stretching unit 200, whereby the absorbent core 40a shrinks, and a flat shape is easily maintained in comparison with a portion at which the absorbent core 40a does not shrink.

On the other hand, the absorbent core 40a that is positioned at the front waistline region or the back waistline region that is positioned outside of the product longitudinal direction than the crotch stretching unit 200 is not shrunk by the crotch stretching unit 200. Therefore, in a state of being retained around the wearer's waist or waistline by the fastening tape, the crotch stretching unit 200 that is maintained in a flat shape at the crotch portion of the disposable diaper does not excessively come into intimate contact with the body, and as a result, the crotch stretching unit 200 is appropriately disposed along the body.

Also, in a case where the crotch stretching unit 200 is stretchable along the product longitudinal direction L, the front waistline region 20 and the back waistline region 30 are easily risen up due to the shrink of the crotch stretching unit 200, and at the time of wearing, a crotch region which is flat along the body can be formed at the wearer's crotch portion.

As a result, the front waistline region 20 and the back waistline region 30 are risen up from the crotch stretching unit 200 and thus the fitting property of the disposable diaper 10 is improved.

That is, the disposable diaper 10 can be stably worn so that the crotch region 25 of the disposable diaper 10 is disposed at the wearer's crotch portion due to the shrink of the crotch stretching unit 200.

Further, the crotch stretching unit 200 may be structured so as to run across the center O1 of the disposable diaper 10 in the product longitudinal direction L and extend to the front waistline region 20 side and the back waistline region 30 side.

Furthermore, the center O2 of the crotch stretching unit 200 in the product longitudinal direction L is disposed at the front waistline region 20 side than the center O1 of the disposable diaper 10 in the product longitudinal direction L.

On the other hand, in a case where movement of the wearer has arisen (in particular, when the wearer lifts his or her legs at the laydown posture, stands up or sits down), the stretching quantity of the skin on the surface of the wearer's body (the variation quantity of the length) is greater in ventral side (buttocks part) than in dorsal side.

The center O2 of the crotch stretching unit 200 in the product longitudinal direction L is disposed at the front waistline region 20 side than the center O1 of the disposable diaper 10 in the product longitudinal direction L, whereby the length in the product longitudinal direction L of the back waistline region 30 in a natural state of the disposable diaper 10 can be larger than the length in the product longitudinal direction L of the front waistline region 20. Therefore, even in the case where the movement of the wearer has arisen, it is possible to restrain a circumstance that the front waistline region 20 and the back waistline region 30 of the disposable diaper 10 move in an orientation along the product longitudinal direction L.

It is to be noted that the crotch stretching unit 200 is preferably configured by a stretchable sheet member.

By making the crotch stretching unit 200 from the stretchable sheet member, the absorbent core 40a in the region in which the stretching sheet member is arranged is uniformly contracted, thereby making it easier to maintain a flat shape. It is to be noted that the stretchable sheet member may be made from, for example, a similar stretchable sheet to that of the leg stretching unit 75.

Also, in place of the elastic sheet as mentioned above, a plurality of yarn-shaped or belt-shaped elastic members made of a polyurethane elastic fiber or a natural rubber are disposed, whereby the crotch stretching unit 200 may be structured. In this case, in order to uniformly shrink the absorbent core 40a by the crotch stretching unit 200, it is preferable that intervals between elastic members be 7 mm or less or it is more preferable that the intervals be 5 mm or less. In addition, in order to uniformly shrink the absorbent core 40a, it is desirable that a difference in intervals of the elastic members adjacent to each other be 2 mm or less.

The stretch rate of the crotch stretching unit 200 is specifically, preferably 1.2 times to 1.8 times. For example, in the present embodiment, the stretch rate of the crotch stretching unit 200 set to 1.4 times. A ratio of expansion and contraction means degree of expansion and contraction (product longitudinal direction L) of the crotch stretching unit 200 and is determined as follows.

A ratio of expansion and contraction means degree of expansion and contraction (product longitudinal direction L) of the crotch stretching unit 200 and is determined as follows.

Ratio of expansion and contraction=(length in the expansion and contraction direction of the crotch stretching unit 200 in the maximum stretched state)/(length in the expansion and contraction direction of the crotch stretching unit 200 in a natural state)

It is to be noted that the measurement of ratio of expansion and contraction is the same as the leg stretching unit of the above, description thereof will be omitted.

By thus setting the stretch rate of the crotch stretching unit 200 to 1.2 times to 1.8 times, it is possible to favorably follow the stretching of the skin of the wearer.

For example, when the wearer is slouchy such that the front side of the body is cringing, the skin at the side of the hip portion of the wearer stretches by approximately 30% as compared to the state when the body has been stretched out.

Namely, if a stretch rate of the crotch stretching unit 200 is 1,2 times or less, a shrinkage of the crotch stretching unit 200 in a natural state is not sufficient in degree; a shrinkage in an absorber disposition region in the crotch unit of the disposable diaper 10 is small in degree in comparison with a case in which the crotch stretching unit 200 is not provided; it becomes insufficient for the crotch unit of the disposable diaper 10 to form a flat shape so as to be taken along the body at the wearer's crotch.

On the other hand, when the stretch rate of the crotch stretching unit 200 is more than 1.8 times, the contraction size in the contraction direction of the crotch stretching unit 200 becomes too large, because of which the region where the crotch stretching unit 200 exists easily comes in close contact with the body of the wearer rather than running along it, and the disposable diaper 10 easily shifts to the lower side of the wearer.

Also, the amount of shrinkage in the product longitudinal direction L of the crotch stretching unit 200 may be configured so as to be 2% to 8% of a length in the product longitudinal direction L of the disposable diaper 10.

It is to be noted that the amount of shrinkage is a difference between a length "b (mm)" in a stretched state to an extent such that wrinkles become sufficiently small and a surface of a sample is close to be smooth and a length "a (mm)" in a natural state in an orientation along the stretching direction of the sample, and this amount can be computed by (b–a).

The Inventor successfully verified that, when the amount of shrinkage in the product longitudinal direction L of the crotch stretching unit 200 is 2% to 8% of the length in the product longitudinal direction L of the disposable diaper 10, in the course of attaching the disposable diaper 10 to the wearer, the crotch stretching unit 200 is easily preferably taken along the wearer's body.

Here, if the amount of shrinkage in the product longitudinal direction L of the crotch stretching unit 200 is larger than 8%, the crotch stretching unit 200 shrinks too much; the length in the product longitudinal direction L of the disposable diaper 10 is insufficient; it becomes difficult to wear the disposable diaper 10 on the wearer's body; or alternatively, the disposable diaper 10 and the wearer's body excessively come into intimate contact with each other at the crotch region 25, and are easily displaced from each other.

On the other hand, if the amount of shrinkage in the product longitudinal direction L of the crotch stretching unit 200 is 2% or less, it becomes difficult to attain an advantageous effect of the crotch stretching unit 200 itself that the disposable diaper 10 is brought into close contact with the wearer's body.

Furthermore, a center of the crotch stretching unit 200 in the product longitudinal direction L is arranged closer to the side of the front waistline region 20 as compared to a center of the disposable diaper 10 in the product longitudinal direction L. Furthermore, the crotch stretching unit 200 is arranged so as to span the center of the disposable diaper 10 in the product longitudinal direction L.

In such a case, in consideration of the rigidity of the absorbent core 40a and the rigidity of other components making up the disposable diaper 10, the thickness or arrangement pitch can be arbitrarily selected for an elastic member to be used. However, it is preferable to make the entire region of side edge unit in the product widthwise direction W of the absorbent core 40a be in a contracted state at the time when a main body of the disposable diaper 10 is made in a natural state (non-stretched state).

Also, in the crotch region 25 of the absorber 40, a notch 115 (a notch 125) is formed. The notch 115 and the notch 125 are regions in which the absorbent core 40a constituting the absorber 40 does not exist. In the embodiment, the notch 115 and the notch 125 come under low rigidity portions at which a basis weight of the absorbent core 40a is lower than that of any other portion of the absorbent core 40a. It is to be noted that, in place of forming the notch 115 and the notch 125, regions of the notch 115 and the notch 125 may be such that the basis weight of the absorbent core 40a is lower than that of any other portion of the absorbent core 40a.

The notch 115 and the notch 125 exist along an edge in the product longitudinal direction L of the crotch stretching unit 200. Incidentally, it is preferable that, even if the notch 115 and the notch 125 are formed, the absorbent core 40a that is positioned in the front waistline region 20 and the back waistline region 30 and the absorbent core 40a that is positioned in the crotch region 25 are continuous in the product widthwise direction, in particular, without being completely being separated from each other.

As the notch 115 and the notch 125 run towards the outer side of the product widthwise direction W, the length in the product longitudinal direction L (natural state of the disposable diaper 10) keeps on widening. As a result of such a shape, the outer side of the product widthwise direction W of the absorbent core 40a can constrict easily, and thus, a flat "bottom unit" is formed in the disposable diaper 10. Furthermore, the absorbent core 40a positioned towards the front waistline region 20 from the notch 115, and the absorbent core 40a positioned towards the back waistline region 30 from the notch 125 rise up from the "bottom unit", and can easily curve along the roundness of the body of the wearer (the abdomen and the hip).

The edge towards the front waistline region 20 (back waistline region 30) of the notch115 (notch125) is arc shaped. The shape of the edge of the notch115 (notch125) is such that the center of the arc is positioned in the back waistline region 30 (front waistline region 20) from the edge. As a result of such a shape, the deformation along the roundness of the body of the wearer occurs more easily and remarkably.

A width of the crotch stretching unit 200 in the product widthwise direction W is ½ or more of a width of the absorbent core 40a in the product widthwise direction W in a region in which the crotch stretching unit of the absorbent core 40a exists.

Therefore, a predetermined width or more of a site at which the absorbent core 40a has been disposed is shrunk by the crotch stretching unit 200, whereby the absorbent core 40a is shrunk, and the absorbent core 40a is lifted up so as to approach the wearer's body.

Such lifting up of the absorbent core 40a is achieved in the crotch region, whereby a gap between the disposable diaper 10 and the wearer can be reduced. In a case where the width of the crotch stretching unit 200 in the product widthwise direction W is 60% or less of the width of the absorber 40 (the absorbent core 40a) in the product widthwise direction, or alternatively, in a case where the width is 80% or more, the gap between the disposable diaper 10 and the wearer can be further reduced.

If the width of the crotch stretching unit 200 is too small in comparison with the width of the absorbent core 40a, an advantageous effect of lifting up the absorbent core 40a as mentioned above is hardly attained. On the other hand, if the width of the crotch stretching unit 200 is too large in comparison with the width of the absorbent core 40a, the disposable diaper 10 is worn in a state in which a site at which the absorbent core 40a is not disposed shrinks than a site at which the absorbent core 40a is disposed. In this manner, members constituting the site at which the absorbent core 40a is not disposed overlap with each other, the crotch stretching unit 200 hardens, and the comfort in wearing the disposable diaper 10 is degraded.

For example, in a case where a dimension of the narrowest site (in the stretched state) is 120 mm in a region in which the crotch stretching unit of the absorbent core 40a exists, it is preferable that the width of the crotch stretching unit 200 be 60 mm to 110 mm. More preferably, it is preferable that the width of the crotch stretching unit 200 be 90 mm to 110 mm.

It is preferable that the site at which the width of the absorbent core 40a is the smallest in the product widthwise direction W be provided at the front side by 10 mm to 60 mm with respect to the centerline of the product longitudinal direction. Preferably, the site at which the width of the absorbent core 40a is the smallest in the product widthwise direction is provided at the front side by 20 mm to 40 mm with respect to the centerline of the product longitudinal direction. It is preferable that the crotch stretching unit 200 be formed so as to run across the site at which the width of the absorbent core 40a is the smallest in the product widthwise direction W.

A position at which the left and right femoral parts of the wearer are the most proximal to each other is a front side than a center in the forward and backward direction of the wearer's body. Therefore, due to the shrink force of the crotch stretching unit 200, the site at which the width of the absorbent core 40a is the smallest in the product widthwise direction W can be actively disposed at the position at which the left and right femoral parts of the wearer are the most proximal to each other. In other words, even if a wearing assistant such as the wearer's mother does not carry out alignment of the absorbent core 40a, the alignment of the absorbent core 40a is naturally carried out.

4. Method of manufacturing disposable diaper

Next, an example of a method of manufacturing the absorbent article according to the present embodiment is explained. As far as the method that is not described in the present embodiment is concerned, the existing method can be used. Furthermore, the manufacturing method explained below is only an example, and the absorbent article can also be manufactured by other manufacturing methods. The method of manufacturing the absorbent article includes at least a component-forming step, a component-loading step, a leg-hole-forming step, and a cutting step.

In the component-forming step, components configuring the absorbent article are formed. Specifically, for example, an absorbent material configuring the absorber is deposited to form the absorber 40.

In the component-loading step, stretchable sheets constituting the leg stretching unit 75; other webs such as webs constituting the topsheet; and components constituting the disposable diaper 10 such as the leakage preventing sheet, the absorber, the leg stretching unit 75, and the buttocks part stretching unit 77 are loaded on the webs constituting the backsheet.

In the leg-hole-forming step, the topsheet 50, the exterior sheet 60, and the backsheet 60a are cut. In this manner, a front end 77F of the buttocks part stretching unit 77 is cut, and the leg opening unit 35 that is disposed around the wearer's leg-hole is formed.

In the cutting step, a continuous body in which the topsheet 50, the backsheet 60a, the absorber 40 are arranged is cut into a size of a single product ing the product widthwise direction W. In this manner, the disposable diaper 10 is manufactured.

5. Other Embodiments

As described above, although the contents of the present invention were disclosed through the embodiments of the present invention, it is not to be understood that the statements and drawings forming a part of this disclosure limit the present invention. From this disclosure, a variety of alternate modes, examples, and operational techniques would be self-evident to one skilled in the art.

The leg stretching unit 75 may be coincident with a joint portion of the leg side gather in the product widthwise direction or may be disposed at the inside of the product widthwise direction than the joint portion of the leg side gather. The number of elastic members constituting the leg stretching unit 75 and the buttocks part stretching unit 77 may be one or may be two or more.

Also, although the foregoing embodiment described the disposable diaper of open type by way of example, the present invention can also be applied to a disposable diaper of pants type. Both of the left and right side edges of the outer layer sheet forming the front waistline region and the back waistline region are joined with each other, whereby, in the diaper of pants type having the waistline opening unit and a pair of leg opening units, the outer layer sheets of the front waistline region and the back waistline region has elastic elements which are shrinkable and stretchable in the product widthwise direction W, and by shrinking these elastic elements, the disposable diaper is retained around the wearer's waistline. Namely, a region in which both of the left and right edges extending in the product longitudinal direction L is obtained as a waistline retaining unit.

As described above, needless to say, the present invention includes various embodiments and the like not described here. Accordingly, the scope of the present invention is defined only by the appended claims in view of the above description.

It is to be noted that all the contents of Japanese Patent Application No. 2012-259110 (which was filed on Nov. 27, 2012) are incorporated in the present specification by reference.

INDUSTRIAL APPLICABILITY

It is possible to provide a disposable diaper which is capable of preventing involvement of an end in a product widthwise direction at the time of wearing the disposable diaper while appropriately covering a buttocks part.

REFERENCE SIGNS LIST

10 . . . Disposable diaper
20 . . . Front waistline region
25 . . . Crotch region
30 . . . Back waistline region
35 . . . Leg opening unit 35I . . . Inside end
35F . . . Foreside leg opening unit
35R . . . Backside leg opening unit
40 . . . Absorber
40a . . . Absorbent core
40b . . . Core wrap
50 . . . Topsheet
60 . . . Exterior sheet
60a . . . Backsheet
70 . . . Side flaps
75 . . . Leg stretching unit
77 . . . Buttocks part stretching unit
77F . . . Front end
80 . . . Leg side gather
81 . . . Elastic member
85 . . . Waistline stretching unit
90 . . . Fastening tape
91 . . . Base sheet
92 . . . Hook sheet
95 . . . Target unit
115 . . . Notch
125 . . . Notch
200 . . . Crotch stretching unit
L . . . Product longitudinal direction
W . . . Product widthwise direction

The invention claimed is:
1. A disposable diaper, comprising:
a front waistline region;
a back waistline region; and
a crotch region positioned between the front waistline region and the back waistline region;
a product longitudinal direction oriented from the front waistline region to the back waistline region;
a product widthwise direction orthogonal to the product longitudinal direction:
an absorber running across the crotch region and extending to at least one of the front waistline region and the back waistline region;
a pair of side flaps extending across the front waistline region, the crotch region, and the back waistline region, said pair of side flaps being disposed on opposite sides of the absorber in the product widthwise direction; and
a pair of fastening tapes each extending, in the product widthwise direction, in the back waistline region outward of the pair of side flaps, respectively, said pair of fastening tapes being releasably attachable to the front waistline region;
wherein
each side flap of the pair of side flaps has:
a lateral edge including an leg opening unit concave toward a center of the absorber in the product widthwise direction, said leg opening unit having a center in the product longitudinal direction;
a leg stretching unit disposed inward of the leg opening unit in the product widthwise direction and stretchable in the product longitudinal direction; and
a buttocks part stretching unit running across the crotch region and the back waistline region, and stretchable in the product longitudinal direction;
the leg opening unit in said each side flap has:
a backside leg opening unit positioned backward of the center of the leg opening unit in the product longitudinal direction; and
a foreside leg opening unit positioned forward of the center of the leg opening unit in the product longitudinal direction,
wherein an area between the backside leg opening unit and a straight line, which passes through the center of the absorber in the product widthwise direction and which is parallel to the product longitudinal direction, is larger than an area between the foreside leg opening unit and the straight line, and
in said each side flap,
said buttocks part stretching unit is disposed outward of the leg stretching unit in the product widthwise direction,
a front end of the buttocks part stretching unit is positioned backward of the center of the leg opening unit in the product longitudinal direction and reaches the lateral edge of the side flap, and
a plurality of convex units convex away from the absorber in the product widthwise direction is formed only in the backside leg opening unit and outward of the front end of the buttocks part stretching unit in the product widthwise direction.
2. The disposable diaper according to claim 1, wherein the disposable diaper has a center in the product longitudinal direction, and
in said each side flap, a center of the leg stretching unit in the product longitudinal direction and the center of the leg opening unit in the product longitudinal direction each are positioned forward of the center of the disposable diaper in the product longitudinal direction.
3. The disposable diaper according to claim 1, wherein in said each side flap, a distance between the buttocks part stretching unit and the leg stretching unit in the product widthwise direction is 10 mm to 30 mm.
4. The disposable diaper according to claim 1, wherein in said each side flap,
the leg opening unit includes an innermost point in the product widthwise direction, and
a distance between the innermost point of the leg opening unit and the leg stretching unit is shorter than a distance between the leg stretching unit and the buttocks part stretching unit, and is 15 mm or less.
5. The disposable diaper according to claim 4, wherein in said each side flap, the innermost point of the leg opening unit is positioned on a centerline, which extends in the product longitudinal direction and passes through a center in the product widthwise direction between the leg stretching unit and the buttocks part stretching unit.
6. The disposable diaper according to claim 1, wherein in said each side flap, a concave unit concave toward the absorber in the product widthwise direction is formed in the foreside leg opening unit.
7. The disposable diaper according to claim 1, wherein in said each side flap,
a rear end of the buttocks part stretching unit and a rear end of the leg stretching unit are positioned in the back waistline region and are flush with each other in the product widthwise direction.
8. The disposable diaper according to claim 1, wherein in said each side flap,
a length of the leg stretching unit in the product longitudinal direction is greater than a length of the buttocks part stretching unit in the product longitudinal direction.
9. The disposable diaper according to claim 1, further comprising:
an exterior sheet; and
a back sheet disposed between (i) the pair of side flaps and (ii) the exterior sheet in a product thickness direction perpendicular to the product widthwise direction and the product longitudinal direction, wherein said each side flap further includes a farther leg stretching unit adjacent to said leg stretching unit in the product widthwise direction, in said each side flap, said further leg stretching unit is directly sandwiched between the back sheet and the exterior sheet in the product thickness direction, and in said each side flap, said leg stretching unit and the buttocks part stretching unit are directly sandwiched between the side flap and the exterior sheet in the product thickness direction.

10. The disposable diaper according to claim 1, wherein in the foreside leg opening unit of said each side flap, no stretchable units reach the lateral edge of the side flap, and the buttock part stretching unit of said each side flap is spaced apart from the corresponding fastening tape in the product widthwise direction.

\* \* \* \* \*